(12) United States Patent
King et al.

(10) Patent No.: US 11,258,964 B2
(45) Date of Patent: *Feb. 22, 2022

(54) SYNTHESIZING SPATIALLY-AWARE TRANSITIONS BETWEEN MULTIPLE CAMERA VIEWPOINTS DURING MINIMALLY INVASIVE SURGERY

(71) Applicant: Covidien LP, Mansfield, MA (US)

(72) Inventors: Daniel R. King, Jacksonville, FL (US); Dwight Meglan, Westwood, MA (US); Arvind K. Ramadorai, Lexington, MA (US)

(73) Assignee: COVIDIEN LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/065,580

(22) Filed: Oct. 8, 2020

(65) Prior Publication Data

US 2021/0029307 A1 Jan. 28, 2021

Related U.S. Application Data

(63) Continuation of application No. 16/636,075, filed as application No. PCT/US2018/000291 on Aug. 16, 2018, now Pat. No. 10,834,332.

(Continued)

(51) Int. Cl.
*H04N 5/262* (2006.01)
*A61B 34/30* (2016.01)
(Continued)

(52) U.S. Cl.
CPC .......... *H04N 5/2628* (2013.01); *A61B 34/30* (2016.02); *A61B 90/06* (2016.02); *A61B 90/361* (2016.02);
(Continued)

(58) Field of Classification Search
CPC ...... H04N 5/2628; H04N 5/247; A61B 34/30; A61B 90/06; A61B 90/361; G06T 7/70
See application file for complete search history.

(56) References Cited

U.S. PATENT DOCUMENTS 7,843,451 B2 11/2010 Lafon
8,398,541 B2* 3/2013 DiMaio .................. A61B 34/70
600/111

(Continued)

FOREIGN PATENT DOCUMENTS

| WO | 2011040769 A2 | 4/2011 |
| WO | 2013009510 A2 | 1/2013 |
| WO | 2017062393 A2 | 4/2017 |

OTHER PUBLICATIONS

International Search Report and Written Opinion dated Jan. 2, 2019 corresponding to counterpart Int'l Patent Application PCT/US18/000291.

(Continued)

*Primary Examiner* — Mishawn N. Hunter

(57) ABSTRACT

Disclosed are systems, devices, and methods for synthesizing spatially-aware transitions between camera viewpoints. An exemplary method includes receiving images of a surgical site from a first camera, tracking a position of a robotic arm including a second camera coupled thereto, tracking the pose of the second camera, receiving images of the surgical site from the second camera that are different from the images received from the first camera as the robotic arm is moved to different positions, comparing a pose from which at least one of the images received from the second camera were captured to a pose from which at least one of the images received from the first camera were captured, generating a transition between the compared images, and (Continued)

displaying the transition when switching between displaying images received from the first and second cameras.

27 Claims, 3 Drawing Sheets

Related U.S. Application Data

(60) Provisional application No. 62/546,273, filed on Aug. 16, 2017.

(51) Int. Cl.
    *A61B 90/00*     (2016.01)
    *G06T 7/70*     (2017.01)
    *H04N 5/247*     (2006.01)

(52) U.S. Cl.
    CPC .............. *G06T 7/70* (2017.01); *H04N 5/247* (2013.01); *A61B 2090/061* (2016.02); *A61B 2090/371* (2016.02); *G06T 2207/30244* (2013.01)

(56) References Cited

U.S. PATENT DOCUMENTS

| | | | |
|---|---|---|---|
| 8,769,395 B2 | 7/2014 | Boliek et al. | |
| 8,868,338 B1 | 10/2014 | Chau et al. | |
| 8,902,282 B1 | 12/2014 | Zhu | |
| 8,982,154 B2 | 3/2015 | Vincent et al. | |
| 9,188,973 B2 | 11/2015 | Tenney | |
| 9,699,445 B2 * | 7/2017 | Hoffman | H04N 13/366 |
| 10,070,940 B2 * | 9/2018 | Bailey | A61B 90/10 |
| 10,285,765 B2 | 5/2019 | Sachs | |
| 10,834,332 B2 | 11/2020 | King et al. | |
| 2009/0259102 A1 | 10/2009 | Koninckx et al. | |
| 2013/0050069 A1 | 2/2013 | Ota | |
| 2014/0163736 A1 | 6/2014 | Azizian et al. | |
| 2014/0288413 A1 | 9/2014 | Hwang et al. | |
| 2015/0045657 A1 | 2/2015 | Kim | |
| 2017/0027650 A1 | 2/2017 | Merck et al. | |
| 2017/0143442 A1 | 5/2017 | Tesar | |
| 2017/0258526 A1 | 9/2017 | Lang | |
| 2018/0243045 A1 | 8/2018 | Franjic | |
| 2018/0368656 A1 | 12/2018 | Austin | |
| 2019/0088162 A1 | 3/2019 | Meglan | |

OTHER PUBLICATIONS

Extended European Search Report dated Apr. 15, 2021 corresponding to counterpart Patent Application EP 18846551.2.

* cited by examiner

SYNTHESIZING SPATIALLY-AWARE TRANSITIONS BETWEEN MULTIPLE CAMERA VIEWPOINTS DURING MINIMALLY INVASIVE SURGERY

CROSS-REFERENCE TO RELATED APPLICATIONS

This application is a Continuation application which claims the benefit of and priority to U.S. patent application Ser. No. 16/636,075, filed on Feb. 3, 2020, which is a National Stage Application of PCT Application Serial No. PCT/US2018/000291 under 35 USC § 371 (a), filed Aug. 16, 2018, which claims benefit of and priority to U.S. Provisional Patent Application Ser. No. 62/546,273, filed Aug. 16, 2017, the disclosures of each of the above-identified applications are hereby incorporated by reference in their entirety.

BACKGROUND

Robotic surgical systems are increasingly being used in minimally invasive medical procedures. Typically, robotic surgical systems include a surgeon console located remote from one or more robotic arms to which surgical instruments are coupled. The surgeon console may be located on another side of the operating room from the robotic arms, in another room, or in another building, and includes input handles or other input devices for receiving inputs from a surgeon. The inputs are communicated to a central controller, which translates the inputs into commands for manipulating the robotic arms in the vicinity of a patient, for example, within a surgical site.

To provide a view of the surgical site, one or more cameras, which may be included on probes attached to the distal end of one or more of the robotic arms, transmit images to a display at the surgeon console for viewing. Thus, when the probe including the camera is inserted into the patient, image data of the patient's body is displayed on the display. Additional cameras may be positioned outside of the patient, for example, over an incision area, and/or in various locations around the operating room.

Although the inclusion of multiple cameras is extremely useful for providing different views of the surgical site, under certain circumstances, the surgeon may not be able to easily ascertain the pose of the camera from which an image is displayed in relation to the surgical site.

SUMMARY

The present disclosure addresses this issue by providing a method for synthesizing spatially aware transitions between multiple camera viewpoints as used during the surgical procedure. In this regard, a method of transitioning between camera viewpoints during a robotic surgical procedure is provided in accordance with the present disclosure.

In an aspect of the present disclosure, the method includes receiving images of a surgical site from a first camera during the robotic surgical procedure, tracking a position of a robotic arm including a second camera coupled thereto based on data obtained from at least one pose detection sensor tracking the pose of the second camera, receiving images of the surgical site from the second camera that are different from the images received from the first camera as the robotic arm is electromechanically moved to different positions, comparing a pose from which at least one of the images received from the second camera were captured to a pose from which at least one of the images received from the first camera were captured based on the determined pose of the second camera and a predetermined pose of the first camera, generating a transition between the compared images based on a difference in the pose from which the images received from the first and second cameras were captured, and displaying the transition when switching between displaying images received from the first and second cameras.

In another aspect of the present disclosure, the tracking includes determining a pose of the second camera by analyzing configuration settings.

In a further aspect of the present disclosure, tracking includes determining a pose of the second camera based on the images received from the first camera and the images received from the second camera, respectively.

In another aspect of the present disclosure, at least part of the images received from the first camera and at least part of the images received from the second camera overlap.

In a further aspect of the present disclosure, the images received from the first camera and the images received from the second camera are fully distinct.

In another aspect of the present disclosure, generating the transition further includes zooming out from a first viewpoint to an intermediate viewpoint showing a patient's body, and zooming in from the intermediate viewpoint to a second viewpoint.

In a further aspect of the present disclosure, generating the transition further includes synthesizing the images received from the first camera and the images received from the second camera with images of a model of the patient's body.

In another aspect of the present disclosure, the images of the model of the patient's body are based on images obtained during a scan of the patient's body.

In a further aspect of the present disclosure, the method further includes determining a pose of a third camera by tracking the position of a robotic arm including the third camera coupled thereto based on data obtained from at least one pose detection sensor tracking the pose of the third camera, receiving images of the surgical site from the third camera that are different from the images received from the first and second cameras, comparing a pose from which at least one of the images received from the third camera were captured to a pose from which at least one of the images received from the second camera were captured based on the determined pose of the third camera and the determined pose of the second camera, generating a transition between the compared images based on a difference in the pose from which the images received from the second and third cameras were captured, and displaying the transition when switching between displaying images received from the second and third cameras.

In another aspect of the present disclosure, the first camera is positioned between the second camera and the third camera, and generating the transition further includes synthesizing the images received from the first, second, and third cameras such that the transition indicates the pose of the second camera relative to the pose of the first camera and the pose of the third camera.

In an aspect of the present disclosure, a system for transitioning between camera viewpoints during a robotic surgical procedure includes a surgical robot including a first camera, a second camera, and robotic arms coupling the first and second cameras to the surgical robot, and a computer configured to receive images of a surgical site from the first camera during the robotic surgical procedure, track the position of the robotic arm including the second camera coupled thereto based on data obtained from at least one pose detection sensor tracking the pose of the second camera, receive images of the surgical site from the second camera that are different from the images received from the first camera as the robotic arm is electromechanically moved to different positions, compare a pose from which at least one of the images received from the second camera were captured to a pose from which at least one of the images received from the first camera were captured based on the determined pose of the second camera and a predetermined pose of the first camera, generate a transition between the compared images based on a difference in the pose from which the images received from the first and second cameras were captured, and display the transition when switching between displaying images received from the first and second cameras.

In another aspect of the present disclosure, the tracking includes determining a pose of the second camera by analyzing configuration settings.

In a further aspect of the present disclosure, tracking includes determining a pose of the second camera based on the images received from the first camera and the images received from the second camera, respectively.

In another aspect of the present disclosure, at least part of the images received from the first camera and at least part of the images received from the second camera overlap.

In a further aspect of the present disclosure, the images received from the first camera and the images received from the second camera are fully distinct.

In another aspect of the present disclosure, the computer is further configured to generate the transition by, zooming out from a first viewpoint to an intermediate viewpoint showing a patient's body, and zooming in from the intermediate viewpoint to a second viewpoint.

In a further aspect of the present disclosure, generating the transition further includes synthesizing the images received from the first camera and the images received from the second camera with images of a model of the patient's body.

In another aspect of the present disclosure, the images of the model of the patient's body are based on images obtained during a scan of the patient's body.

In a further aspect of the present disclosure, the system further includes a third camera, and the computer is further configured to determine a pose of the third camera by tracking the position of a robotic arm including the third camera coupled thereto based on data obtained from at least one pose detection sensor tracking the pose of the third camera, receive images of the surgical site from the third camera that are different from the images received from the first and second cameras, compare a pose from which at least one of the images received from the third camera were captured to a pose from which at least one of the images received from the second camera were captured based on the determined pose of the third camera and the determined pose of the second camera, generate a transition between the compared images based on a difference in the pose from which the images received from the second and third cameras were captured, and display the transition when switching between displaying images received from the second and third cameras.

In another aspect of the present disclosure, the first camera is positioned between the second camera and the third camera, and generating the transition further includes synthesizing the images received from the first, second, and third cameras such that the transition indicates the pose of the second camera relative to the pose of the first camera and the pose of the third camera.

In an aspect of the present disclosure, a non-transitory computer-readable medium stores a program including instructions which, when executed by a processor, cause a computer to receive images of a surgical site from a first camera during a robotic surgical procedure, track a position of a robotic arm including a second camera coupled thereto based on data obtained from at least one pose detection sensor tracking the pose of the second camera, receive images of the surgical site from the second camera that are different from the images received from the first camera as the robotic arm is electromechanically moved to different positions, compare a pose from which at least one of the images received from the second camera were captured to a pose from which at least one of the images received from the first camera were captured based on the determined pose of the second camera and a predetermined pose of the first camera, generate a transition between the compared images based on a difference in the pose from which the images received from the first and second cameras were captured, and display the transition when switching between displaying images received from the first and second cameras.

In another aspect of the present disclosure, the tracking includes determining a pose of the second camera by analyzing configuration settings.

In a further aspect of the present disclosure, tracking includes determining a pose of the second camera based on the images received from the first camera and the images received from the second camera, respectively.

In another aspect of the present disclosure, at least part of the images received from the first camera and the images received from the second camera overlap.

In a further aspect of the present disclosure, the images received from the first camera and the images received from the second camera are fully distinct.

In another aspect of the present disclosure, the instructions further cause the computer to generate the transition by zooming out from a first viewpoint to an intermediate viewpoint showing a patient's body, and zooming in from the intermediate viewpoint to a second viewpoint.

In a further aspect of the present disclosure, the instructions further cause the computer to synthesize the images received from the first camera and the images received from the second camera with images of a model of the patient's body.

In another aspect of the present disclosure, the images of the model of the patient's body are based on images obtained during a scan of the patient's body.

In a further aspect of the present disclosure, the instructions further cause the computer to determine a pose of the third camera by tracking the position of a robotic arm including the third camera coupled thereto based on data obtained from at least one pose detection sensor tracking the pose of the third camera, receive images of the surgical site from the third camera that are different from the images received from the first and second cameras, compare a pose from which at least one of the images received from the third camera were captured to a pose from which at least one of the images received from the second camera were captured based on the determined pose of the third camera and the determined pose of the second camera, generate a transition between the compared images based on a difference in the pose from which the images received from the second and third cameras were captured, and display the transition when switching between displaying images received from the second and third cameras.

In another aspect of the present disclosure, the first camera is positioned between the second camera and the third camera, and generating the transition further includes synthesizing the images received from the first, second, and third cameras such that the transition indicates the pose of the second camera relative to the pose of the first camera and the pose of the third camera.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

The present disclosure is directed to devices, systems, and methods for synthesizing spatially aware transitions between multiple camera viewpoints. As described in more detail below, a robotic surgical system may be used to perform a surgical procedure on a surgical site of a patient. To assist a clinician, or team of clinicians, operating the surgical robot during the surgical procedure, various cameras may be used. Thus, the robotic surgical system of the present disclosure, for example, generally includes at least one surgical robot including at least two cameras positioned about the surgical site, robotic arms coupling the cameras to the surgical robot, a plurality of sensors coupled to the robotic arms and cameras, and at least one computer connected to the surgical robot. The cameras may be incorporated into the surgical robot, into different types of tools used by or attached to the surgical robot, and/or may be free-standing cameras positioned about the surgical site.

Detailed embodiments of such devices, systems incorporating such devices, and methods using the same are described below. However, these detailed embodiments are merely examples of the disclosure, which may be embodied in various forms. Therefore, specific structural and functional details disclosed herein are not to be interpreted as limiting but merely as a basis for the claims and as a representative basis for allowing one skilled in the art to variously employ the present disclosure in virtually any appropriately detailed structure.

Figure 1:
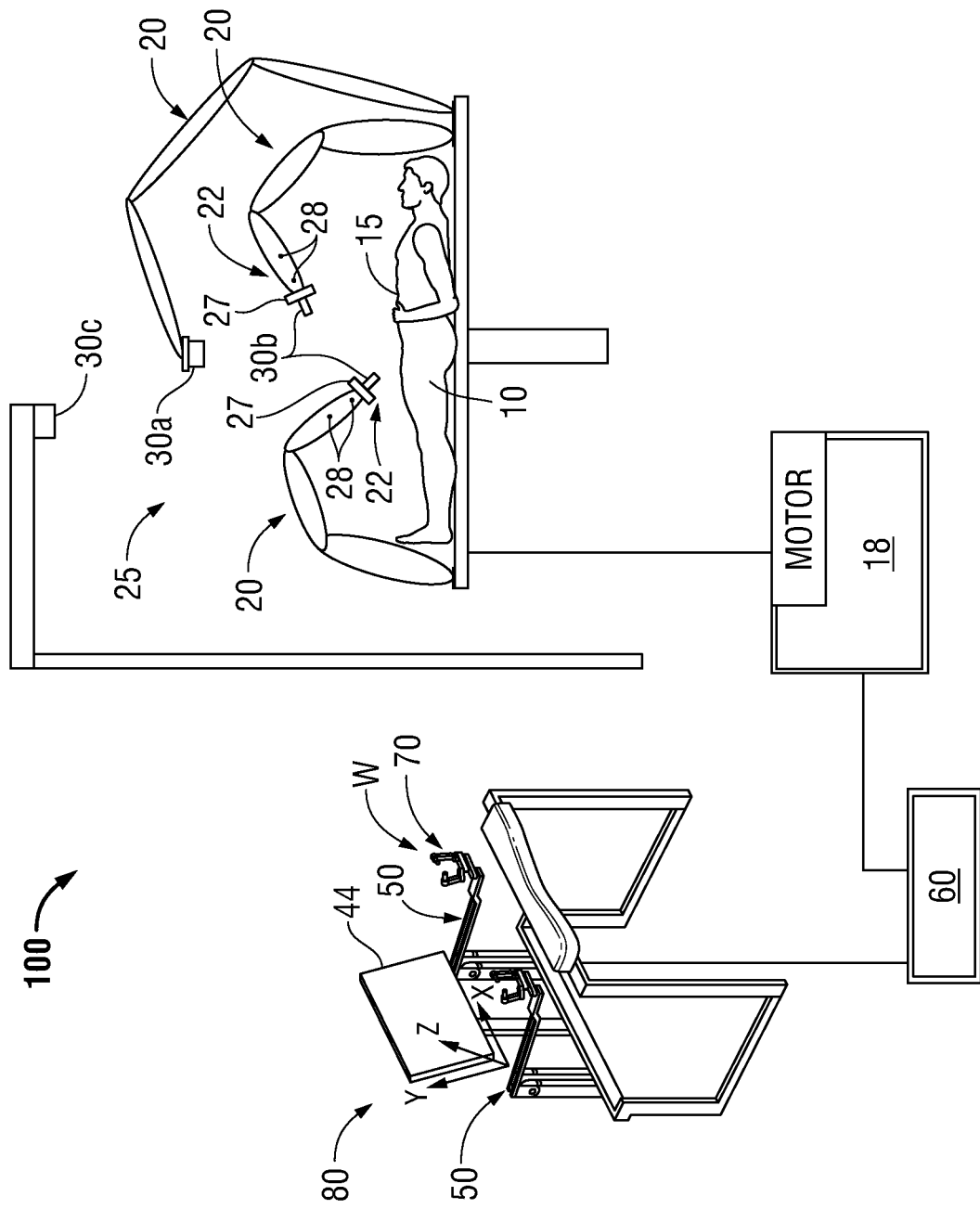
FIG. 1 is a system diagram of an example system for synthesizing spatially-aware transitions between multiple camera viewpoints during a robotic surgical procedure, provided in accordance with an embodiment of the present disclosure.

With reference to FIG. 1, a robotic surgical system 100 is provided in accordance with an embodiment of the present disclosure. Robotic surgical system 100 generally includes a surgical robot 25, a plurality of cameras 30a, 30b, 30c, a controller 60, and a console 80. Surgical robot 25 has one or more robotic arms 20, which may be in the form of linkages, having a corresponding surgical tool 27 interchangeably fastened to a distal end 22 of robotic arm 20. One or more robotic arms 20 may also have fastened thereto a camera 30b and each arm 20 may be positioned about a surgical site 15 around a patient 10. Robotic arm 20 may also have coupled thereto one or more pose detection sensors 28 capable of detecting a position, direction, orientation, and/or angle (referred to collectively hereinafter as "pose"), as well as a speed of movement of robotic arm 20 and/or camera 30b. In some embodiments, the pose detection sensors 28 may be coupled directly to camera 30b or surgical tool 27.

Surgical robot 25 further includes a robotic base 18, which includes one or more motors used to mechanically drive each robotic arm 20 and operate each surgical tool 27. Controller 60 is connected to and configured to control the operations of surgical robot 25 via robotic base 18. Similarly, console 80 is connected to surgical robot 25 either directly, or via a network (not shown). Controller 60 may be integrated into console 80, or may be a separate, stand-alone device connected to console 80 and surgical robot 25 via robotic base 18.

Console 80 is a user interface by which a user, such as a surgeon or clinician, may operate surgical robot 25. Console 80 operates in conjunction with controller 60 to control the operations of surgical robot 25. In some embodiments, console 80 communicates with robotic base 18 through controller 60 and includes a display device 44 configured to display images. In one embodiment, display device 44 displays images of surgical site 15, which may include images captured by camera 30a attached to robotic arm 20, and/or include data captured by cameras 30a, 30b, 30c that are positioned about the surgical theater, (for example, a camera 30b positioned within surgical site 15, a camera 30a positioned adjacent patient 10, and/or a camera 30c mounted to the walls or ceiling of an operating room in which robotic surgical system 100 is used). In some embodiments, cameras 30a, 30b, 30c capture visual images, infra-red images, ultrasound images, X-ray images, thermal images, and/or any other known real-time images of surgical site 15. In embodiments, cameras 30a, 30b, 30c transmit captured images to controller 60, which may create three-dimensional images of surgical site 15 in real-time from the images and transmits the three-dimensional images to display device 44 for display. In another embodiment, the displayed images are two-dimensional images captured by cameras 30a, 30b, 30c.

Console 80 also includes one or more input handles attached to gimbals 70 that allow a surgeon to manipulate robotic surgical system 100 (e.g., move robotic arm 20, distal end 22 of robotic arm 20, and/or surgical tool 27). Each gimbal 70 is in communication with controller 60 to transmit control signals thereto and to receive feedback signals therefrom. Additionally or alternatively, each gimbal 70 may include control interfaces or input devices (not shown) which allow the surgeon to manipulate (e.g., clamp, grasp, fire, open, close, rotate, thrust, slice, etc.) surgical tool 27 supported at distal end 22 of robotic arm 20.

Each gimbal 70 is moveable to move distal end 22 of robotic arm 20 and/or to manipulate surgical tool 27 within surgical site 15. As gimbal 70 is moved, surgical tool 27 moves within surgical site 15. Movement of surgical tool 27 may also include movement of distal end 22 of robotic arm 20 that supports surgical tool 27. In addition to, or in lieu of, a handle, the handle may include a clutch switch, and/or one or more input devices including a touchpad, joystick, keyboard, mouse, or other computer accessory, and/or a foot switch, pedal, trackball, or other actuatable device configured to translate physical movement from the clinician to signals sent to controller 60. Controller 60 further includes software and/or hardware used to operate the surgical robot, and to synthesize spatially aware visually and cognitively appropriate transitions when switching between video images received from cameras 30a, 30b, 30c, as described in more detail below.

Cameras 30a, 30b, 30c may, for example, be monocular and/or stereoscopic binocular cameras, and may be configured to be positioned inside the body of patient 10 to capture images around organs and other structures inside the body of patient 10. Cameras 30a, 30b, 30c may have various viewpoints based on where their respective pose. In embodiments, cameras 30a, 30b, 30c may be positioned such that their respective viewpoints show surgical site 15 from various poses. For example, robotic surgical system 100 may be configured to have a camera 30a positioned directly above and perpendicular to surgical site 15, while other cameras 30b are positioned about surgical site 15 inside the body of patient 10. In some embodiments, one or more cameras 30a, 30b, 30c may be positioned at viewpoints in front of other cameras 30a, 30b, 30c, and one or more cameras 30a, 30b, 30c may be positioned at viewpoints adjacent to other cameras 30a, 30b, 30c. In still further embodiments, some cameras 30a, 30b, 30c may have viewpoints intermediate to the viewpoints of two or more other cameras 30a, 30b, 30c.

It will be appreciated that the pose of the images captured by cameras 30a, 30b, 30c may be mirrored or rotated relative to a view from above patient 10 in accordance with the surgeon's preference. In addition, it will be appreciated that the size of the captured images on display device 44 may be scaled to be larger or smaller than the actual structures of surgical site 15 permitting the surgeon to have a better view of structures within surgical site 15.

Figure 2:
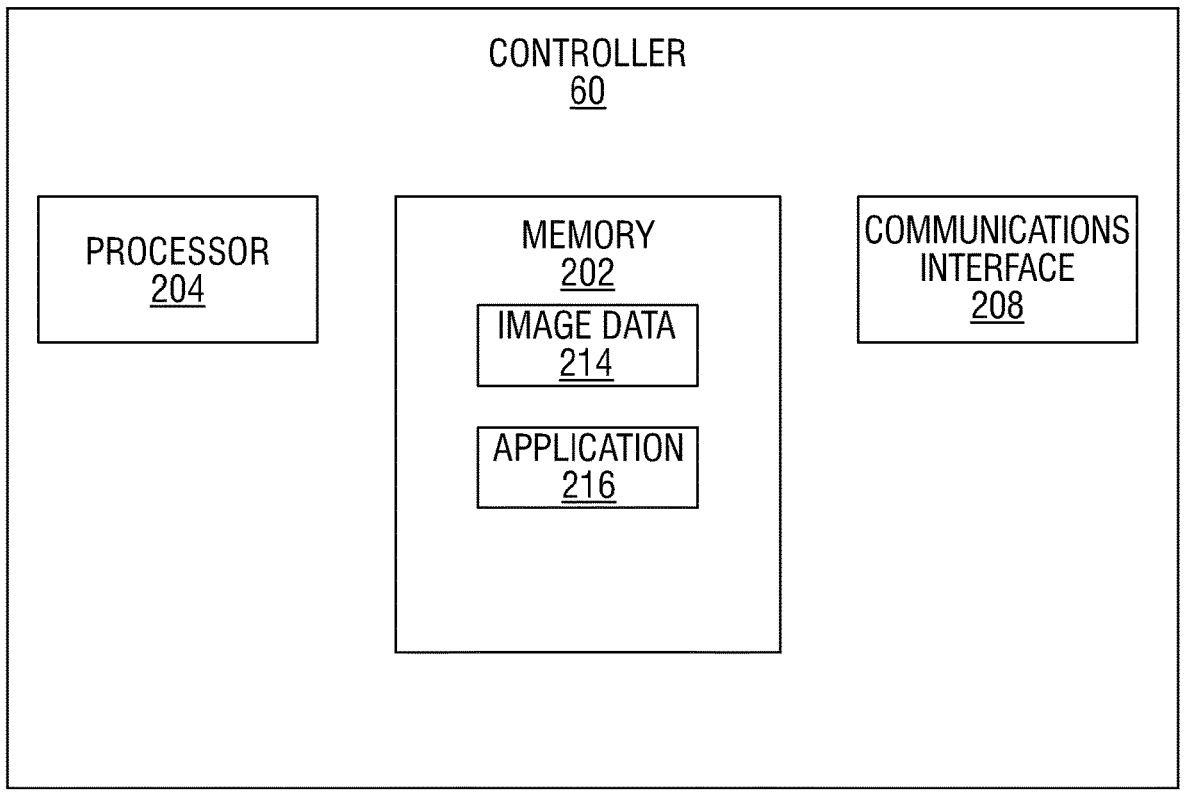
FIG. 2 is a schematic diagram of a console forming part of the system of FIG. 1, provided in accordance with an embodiment of the present disclosure.

Turning now to FIG. 2, there is shown a system diagram of controller 60. Controller 60 may include memory 202, processor 204, and/or communications interface 206.

Memory 202 includes any non-transitory computer-readable storage media for storing data and/or software that is executable by processor 204 and which controls the operation of controller 60. In an embodiment, memory 202 may include one or more solid-state storage devices such as flash memory chips. Alternatively, or in addition to the one or more solid-state storage devices, memory 202 may include one or more mass storage devices connected to processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by processor 204. That is, computer readable storage media includes non-transitory, volatile and non-volatile, removable and non-removable media implemented in any method or technology for storage of information, such as computer-readable instructions, data structures, program modules, and/or other data. For example, computer-readable storage media may include RAM, ROM, EPROM, EEPROM, flash memory, and/or other solid state memory technology, CD-ROM, DVD, Blu-Ray, or other optical storage, magnetic cassettes, magnetic tape, magnetic disk storage, or other magnetic storage devices, and/or any other medium which can be used to store the desired information and which can be accessed by controller 60.

Memory 202 may store an application 216 and/or image data 214. Application 216 may, when executed by processor 204, cause display device 44 of console 80 to present images. Communications interface 206 may be a network interface configured to connect to a network connected to robotic base 18, such as a local area network (LAN) consisting of a wired network and/or a wireless network, a wide area network (WAN), a wireless mobile network, a BLUETOOTH® network, and/or the internet. Additionally or alternatively, communications interface 206 may be a direct connection to robotic base 18.

Figure 3:
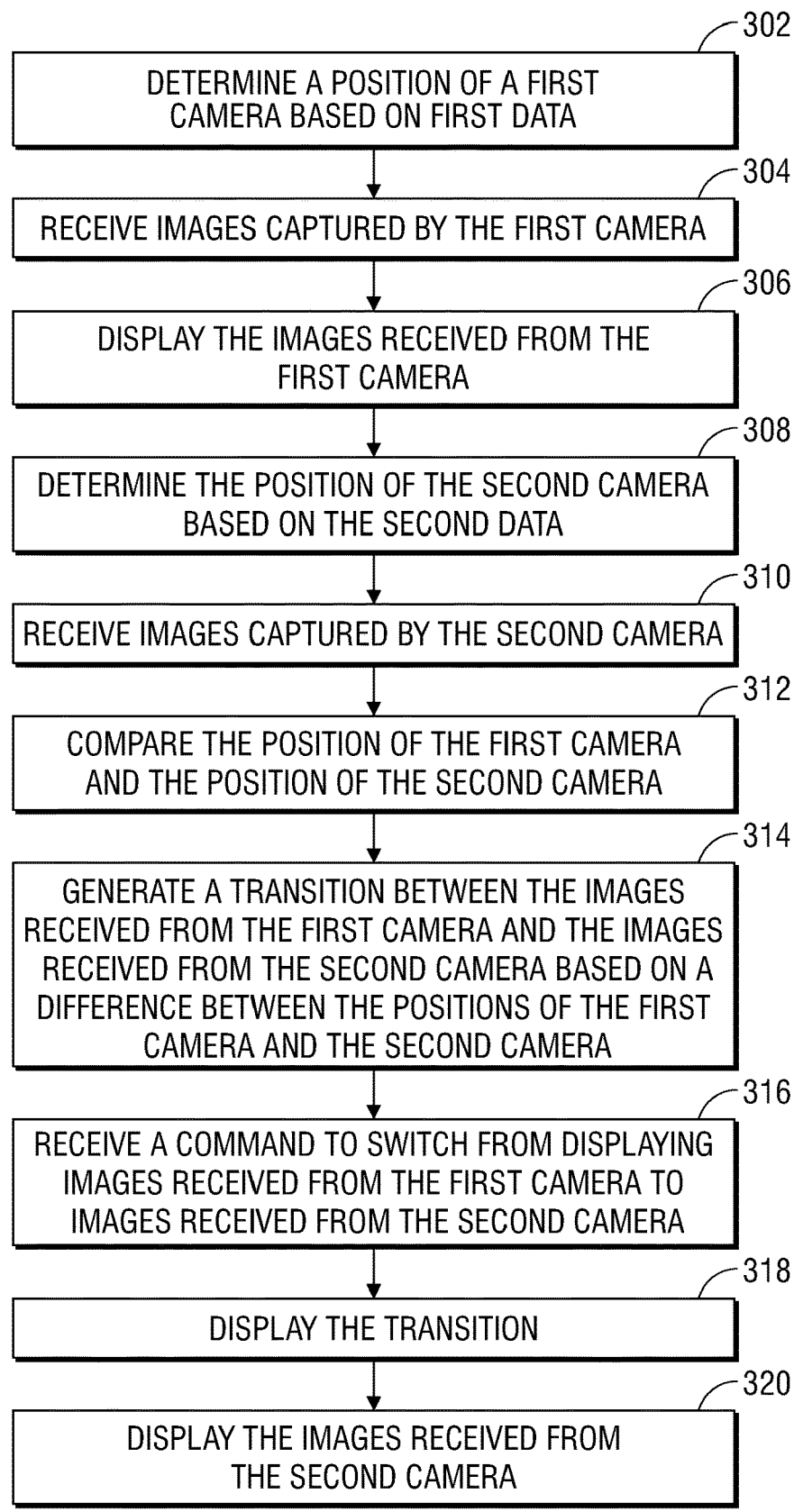
FIG. 3 is a flowchart illustrating an example method of synthesizing spatially aware transitions between multiple camera viewpoints during a robotic surgical procedure, provided in accordance with an embodiment of the present disclosure.

Referring now to FIG. 3, a flowchart is illustrated of an example method 300 for synthesizing spatially aware transitions between multiple camera viewpoints. Method 300 may be performed by, for example, controller 60 and/or console 80 of system 100 shown in FIG. 1. However, for purposes of illustration, the description below will use controller 60 as the device performing method 300.

Starting at step 302, the pose of a first camera 30a, 30b, 30c is determined based on first data. In an embodiment, the first camera 30a, 30b, 30c is located at a fixed position having a predetermined pose, and pose information included in the first data may be stored in configuration settings associated with the first camera 30a, 30b, 30c. In another embodiment, the first data is determined from sensed data received by controller 60. The sensed data includes information related to the pose and movement of a robotic arm attached to the first camera 30a, 30b, 30c and may be collected by one or more sensors, such as a pose detection sensor 28, or other type of sensor. The one or more sensors may be coupled to the robotic arm or attached directly to the first camera 30a, 30b, 30c. In still another embodiment, the first data is determined from the images received by controller 60. In this regard, the images are captured by the first camera 30a, 30b, 30c and transmitted to controller 60. Controller 60 calculates the pose of the first camera 30a, 30b, 30c using algorithms suitable for extracting such information from images captured by the first camera 30a, 30b, 30c. In an embodiment, a global camera 30a, 30c, such as an overhead camera or wide-angle camera with a view point showing the entire operating table vicinity, may provide a frame of reference for the pose of each of the other cameras 30a, 30b, 30c. For example, one or more markers may be included on the one or more other cameras and the global camera may use the markers to determine pose of the other cameras. In another example, two-dimensional projections of the other cameras may be matched with three-dimensional geometric models of the other cameras stored in the memory 202. In still another embodiment, pose of the cameras 30a, 30b, 30c may be determined using linking via ultrasonic source/receiver pairing and/or ultrawide band radio frequency, and the like. In addition to the pose information regarding the first camera 30a, 30b, 30c, the first data may also include information regarding the pose from which the images were captured by the first camera 30a, 30b, 30c. The information regarding the pose from which the images were captured may be determined by the sensors attached to the first camera 30a, 30b, 30c or the robotic arm 20, or may be determined based on the images captured by the first camera 30a, 30b, 30c. In an embodiment, step 302 may be reiterated throughout the usage of robotic surgical system 100.

At step 304, controller 60 receives images captured by the first camera 30a, 30b, 30c, and, at step 306, the received images are displayed on display device 44 of console 80. It will be appreciated that in some embodiments, step 304 may be performed concurrently or before the execution of step 302. For example, the controller 60 receives images captured by the first camera 30a, 30b, 30c and then calculates the pose of the first camera 30a, 30b, 30c from the captured images, which are then displayed on display device 44.

At step 308, the pose of a second camera 30a, 30b, 30c is determined based on second data. In an embodiment, the position of a robotic arm 20 coupled to the second camera 30a, 30b, 30c is tracked based on data obtained from one or more sensors, such as a pose detection sensor 28, or other type of sensor, which may be coupled to the robotic arm 20 or attached directly to the second camera 30a, 30b, 30c. The data from the pose detection sensor 28 includes information related to the pose and movement of a robotic arm 20 attached to the second camera 30a, 30b, 30c. In still another embodiment, the second data is determined from the images received by controller 60, which are captured by the second camera 30a, 30b, 30c and transmitted to controller 60. Controller 60 calculates the pose of the second camera 30a, 30b, 30c using algorithms suitable for extracting such information from images captured by the second camera 30a, 30b, 30c. In addition to the pose information regarding the second camera 30a, 30b, 30c, the second data may also include information regarding the pose from which the images were captured by the second camera 30a, 30b, 30c, which may be determined by the sensors attached to the second camera 30a, 30b, 30c or the robotic arm 20, or may be determined based on the images captured by the second camera 30a, 30b, 30c. In an embodiment, step 308 may be reiterated throughout the usage of robotic surgical system 100.

Thereafter, at step 310, controller 60 receives images captured by the second camera 30a, 30b, 30c. In an embodiment, the images captured by the second camera 30a, 30b, 30c are different from the images received from the first camera 30a, 30b, 30c, indicating that robotic arm 20 is electromechanically moved to a position different than that of the first camera 30a, 30b, 30c. It will be appreciated that in some embodiments, step 308 may be performed concurrently or before the execution of step 310. For example, controller 60 receives images captured by the second camera 30a, 30b, 30c and then calculates the pose of the second camera 30a, 30b, 30c from the captured images.

At step 312, the pose of the first camera 30a, 30b, 30c and the second camera 30a, 30b, 30c are compared to determine a difference in pose from which the images received from the first and second cameras 30a, 30b, 30c were captured. Specifically, controller 60 evaluates the received pose information included in the first and second data to determine the relative pose of the first and second cameras 30a, 30b, 30c, patient 10, and surgical robot 25. In some embodiments, the pose of the first and second cameras 30a, 30b, 30c are determined based on a unified coordinate system. Controller 60 may further determine a difference between the pose from which the images received from the first and second cameras 30a, 30b, 30c were captured.

At step 314, a transition is generated between the images received from the first and second cameras 30a, 30b, 30c, based on the difference between the pose of the first and second cameras 30a, 30b, 30c and/or the difference in the pose from which the images received from the first and second cameras 30a, 30b, 30c were captured. The transition is generated by synthesizing image data received from the first and second cameras 30a, 30b, 30c to create a sequence of images representing the difference in pose between the images received from the first and second cameras 30a, 30b, 30c.

Various techniques are used to convey a sense of change in pose awareness via the transitions, such as zooming in, backing up, moving to the side, swinging over from the pose of one camera 30a, 30b, 30c to the next, and/or panning from one side to the next. For example, if the first camera 30a, 30b, 30c is positioned to a side of the second camera 30a, 30b, 30c, the transition may be generated by producing a sequence of images representing motion blurring according to the difference in pose between the first and second cameras 30a, 30b, 30c to convey a sense of change in pose between the first and second cameras 30a, 30b, 30c. In another example, if the first camera 30a, 30b, 30c is positioned behind the second camera 30a, 30b, 30c, the transition may be generated by producing a sequence of images representing zooming to convey a sense of moving forward from the first camera 30a, 30b, 30c to the second camera 30a, 30b, 30c, or, in an embodiment where there are three or more cameras 30a, 30b, 30c, the transition may be generated by producing a sequence of images representing zooming from the images received from the first camera 30a, 30b, 30c to images received from an intermediate camera 30a, 30b, 30c, and then another sequence of images representing zooming from the images received from the intermediate camera 30a, 30b, 30c to images received from the second camera 30a, 30b, 30c. For example, the images received from the first camera 30a, 30b, 30c may show surgical site 15 from a first viewpoint, the images received from the third camera 30a, 30b, 30c may show the body of patient 10, and the images received from the second camera 30a, 30b, 30c may show surgical site 15 from a second viewpoint. In still another example, the images received from the first and second cameras 30a, 30b, 30c are blended, and, when an overlap is detected between the images received from the first and second cameras 30a, 30b, 30c, a sequence of images are produced that appear to move from the images received from the first camera 30a, 30b, 30c to the images received from the second camera 30a, 30b, 30c in a panning motion. In some embodiments, the images received from the first and second cameras 30a, 30b, 30c may include some overlapping coverage of patient 10, while in other embodiments the images received from the first and second cameras may be fully distinct without any overlapping coverage. For example, the images received from the first and second cameras 30a, 30b, 30c may be displayed as if the images are projected about a geometric object, such as a sphere, centered at or encompassing surgical site 15, such that when viewed by the clinician, the images would have the appearance of a spherical projection of surgical site 15 or an image of surgical site 15 that may be perceived as having visual depth. In another example, images received from an auxiliary camera, i.e., a camera 30a, 30b, 30c with a zoomed-out view point and/or a view point showing the entire surgical site 15, in a rectangular box to provide an overview of surgical site 15. Such an overview may be displayed alongside and/or in conjunction with the images received from the first and second cameras 30a, 30b, 30c.

In still another example, a transition may be augmented by computer-animated graphics to convey a sense of spatial awareness. For example, computer graphical elements may be added to or overlaid onto the images received from the first and second cameras 30a, 30b, 30c to indicate the direction of movement from the pose of the first camera 30a, 30b, 30c and the pose of the second camera 30a, 30b, 30c. In accordance with another embodiment, other images of patient 10 are incorporated into the sequence of images. In an example, the images include a model, such as a geometric model, of the patient's body. In another embodiment, the model of the patient's body is constructed from images obtained during a scan of patient 10 and/or three-dimensional renderings of the body of patient 10. For example, images obtained during a scan, such as magnetic resonance imaging, ultrasound imaging, computed tomography scanning, and the like, are integrated with the images received form the first and second cameras 30a, 30b, 30c, and the sequence of images is produced including the patient body images. In another example, the body of patient 10 may be made to appear transparent or semi-transparent in the transition to convey a sense of pose awareness of the cameras 30*a*, 30*b*, 30*c* within the body of patient 10 and of proximity to organs and/or other structures within the body of patient 10.

Turning now to step 316, controller 60 receives a command to switch from displaying images received from the first camera 30*a*, 30*b*, 30*c* to images received from the second camera 30*a*, 30*b*, 30*c*. The command to switch may be received based on user input, for example, the clinician operating surgical robot 25 via console 80 may press a button to send the command, or may issue a voice command, etc. Alternatively, or in addition, the command may automatically be sent by surgical robot 25 when a particular tool is used such that controller 60 automatically transitions to and displays the images received from a camera 30*a*, 30*b*, 30*c* attached to the surgical tool being used. In some embodiments, steps 312 and 314 are continuously performed throughout the usage of robotic surgical system 100. In other embodiments, steps 312 and 314 are only performed after console 60 receives the command of step 316.

At step 318, display device 44 displays the transition generated at step 314, and then displays the images captured by the second camera 30*a*, 30*b*, 30*c* at step 320. In an embodiment, the controller 60 sends commands to display device 44 to display the images received from the first camera 30*a*, 30*b*, 30*c*, then to display the sequence of images representing the transition, and then to display the images received from the second camera 30*a*, 30*b*, 30*c*.

While the examples and embodiments described above are directed to a system including first and second cameras 30*a*, 30*b*, 30*c*, these examples are not intended to be limiting, and it is envisioned that robotic surgical system 100 may include more cameras 30*a*, 30*b*, 30*c* positioned both inside and outside the body of patient 10.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A method of transitioning between camera viewpoints during a robotic surgical procedure, the method comprising:
  receiving images of a surgical site from a first camera during the robotic surgical procedure;
  tracking a position of a robotic arm including a second camera coupled thereto based on data obtained from tracking a pose of the second camera;
  receiving images of the surgical site from the second camera that are different from the images received from the first camera as the robotic arm is moved to different positions;
  comparing:
    a pose from which at least one of the images received from the second camera was captured; and
    a pose from which at least one of the images received from the first camera was captured based on the determined pose of the second camera and a predetermined pose of the first camera; and
  generating a transition between the compared images based on a difference in the pose from which the images received from the first camera and the images received from the second camera were captured.

2. The method of claim 1, wherein generating the transition further includes:
  zooming out from a first viewpoint to an intermediate viewpoint showing a patient's body; and
  zooming in from the intermediate viewpoint to a second viewpoint, different than the first viewpoint.

3. The method of claim 1, further comprising displaying the transition when switching between displaying images received from the first and second cameras.

4. The method of claim 3, wherein the tracking includes determining a pose of the second camera by analyzing configuration settings.

5. The method of claim 3, wherein the tracking includes determining a pose of the second camera based on:
the images received from the first camera; and
the images received from the second camera.

6. The method of claim 3, wherein at least part of the images received from the first camera and at least part of the images received from the second camera overlap.

7. The method of claim 3, wherein the images received from the first camera and the images received from the second camera are fully distinct.

8. The method of claim 3, wherein generating the transition further includes synthesizing the images received from the first camera and the images received from the second camera with images of a model of the patient's body.

9. The method of claim 8, wherein the images of the model of the patient's body are based on images obtained during a scan of the patient's body.

10. The method of claim 3, further comprising:
determining a pose of a third camera by tracking the position of a further robotic arm including the third camera coupled thereto based on data obtained from tracking the pose of the third camera;
receiving images of the surgical site from the third camera that are different from the images received from the first and second cameras;
comparing:
a pose from which at least one of the images received from the third camera was captured; and
a pose from which at least one of the images received from the second camera was captured based on the determined pose of the third camera and the determined pose of the second camera; and
generating a transition between the compared images based on a difference in the pose from which the images received from the second camera and the images received from the third camera were captured.

11. The method of claim 10, further comprising displaying the transition when switching between displaying images received from the second and third cameras.

12. The method of claim 11, wherein the first camera is positioned between the second camera and the third camera, and wherein generating the transition further includes synthesizing the images received from the first, second, and third cameras such that the transition indicates the pose of the second camera relative to the pose of the first camera and the pose of the third camera.

13. The method of claim 10, wherein the tracking of the position of the further robotic arm is based on data obtained from at least one pose detection sensor.

14. The method of claim 3, wherein the tracking of a position of a robotic arm including the second camera coupled thereto is based on data obtained from at least one pose detection sensor.

15. A system for transitioning between camera viewpoints during a robotic surgical procedure, the system comprising:
a surgical robot including:
a first camera;
a second camera; and
a robotic arm coupling the second camera to the surgical robot; and
a computer configured to:
receive images of a surgical site from the first camera during the robotic surgical procedure;
track a position of the robotic arm, including the second camera coupled thereto, based on data obtained from tracking a pose of the second camera;
receive images of the surgical site from the second camera that are different from the images received from the first camera as the robotic arm is moved to different positions;
compare a pose from which at least one of the images received from the second camera was captured to a pose from which at least one of the images received from the first camera was captured based on the determined pose of the second camera and a predetermined pose of the first camera; and
generate a transition between the compared images based on a difference in the pose from which the images received from the first camera and the images received from the second camera were captured.

16. The system of claim 15, wherein the computer is configured to display the transition when switching between displaying images received from the first camera and displaying images received from the second camera.

17. The system of claim 16, wherein the tracking includes determining a pose of the second camera by analyzing configuration settings.

18. The system of claim 16, wherein tracking includes determining a pose of the second camera based on:
the images received from the first camera; and
the images received from the second camera.

19. The system of claim 16, wherein at least part of the images received from the first camera and at least part of the images received from the second camera overlap.

20. The system of claim 16, wherein the images received from the first camera and the images received from the second camera are fully distinct.

21. The system of claim 16, wherein the computer is further configured to generate the transition by:
zooming out from a first viewpoint to an intermediate viewpoint showing a patient's body; and
zooming in from the intermediate viewpoint to a second viewpoint.

22. The system of claim 16, wherein generating the transition further includes synthesizing the images received from the first camera and the images received from the second camera with images of a model of the patient's body.

23. The system of claim 22, wherein the images of the model of the patient's body are based on images obtained during a scan of the patient's body.

24. The system of claim 16, further comprising a third camera, and wherein the computer is further configured to:
determine a pose of the third camera by tracking the position of a robotic arm including the third camera coupled thereto based on tracking the pose of the third camera;
receive images of the surgical site from the third camera that are different from the images received from the first and second cameras;
compare a pose from which at least one of the images received from the third camera were captured to a pose from which at least one of the images received from the second camera were captured based on the determined pose of the third camera and the determined pose of the second camera;
generate a transition between the compared images based on a difference in the pose from which the images received from the second and third cameras were captured; and display the transition when switching between displaying images received from the second and third cameras.

25. The system of claim 24, wherein the first camera is positioned between the second camera and the third camera, and wherein generating the transition further includes synthesizing the images received from the first, second, and third cameras such that the transition indicates the pose of the second camera relative to the pose of the first camera and the pose of the third camera.

26. The system of claim 24, wherein the computer is further configured to:
  determine a pose of the third camera by tracking the position of a robotic arm including the third camera coupled thereto based on data obtained from at least one pose detection sensor tracking the pose of the third camera.

27. The system of claim 15, wherein a computer configured to:
  track a position of the robotic arm, including the second camera coupled thereto, based on data obtained from at least one pose detection sensor tracking a pose of the second camera.

\* \* \* \* \*